United States Patent
Wentworth et al.

[11] Patent Number: 5,394,090
[45] Date of Patent: Feb. 28, 1995

[54] IMPROVED SYSTEM FOR DETECTING COMPOUNDS IN A GASEOUS SAMPLE USING INDUCED PHOTOIONIZATIONS AND ELECTRON CAPTURE DETECTION

[76] Inventors: Wayne E. Wentworth, Chemistry Dept., University of Houston, Houston, Tex. 77204-5641; Stanley D. Sterns, 1201 Archley Dr., Houston, Tex. 77055

[21] Appl. No.: 201,467

[22] Filed: Feb. 25, 1994

Related U.S. Application Data

[63] Continuation-in-part of Ser. No. 956,632, Oct. 5, 1992, Pat. No. 5,317,271, which is a continuation-in-part of Ser. No. 662,149, Feb. 28, 1991, Pat. No. 5,133,519.

[51] Int. Cl.⁶ .................. G01N 27/62; G01N 27/68
[52] U.S. Cl. .................................. 324/464; 324/455; 73/28.02
[58] Field of Search .......... 324/123 R, 71.4, 449, 324/450, 452, 455, 464; 73/28.02, 23.35; 436/153; 313/231.41, 231.71; 315/111.01, 111.91; 250/379, 385.2

[56] References Cited

U.S. PATENT DOCUMENTS

| | | | |
|---|---|---|---|
| 3,540,851 | 11/1970 | Vree et al. | 324/464 X |
| 3,679,973 | 7/1972 | Smith, Jr. et al. | 324/464 X |
| 4,724,394 | 2/1988 | Langer et al. | 324/464 |
| 4,851,683 | 7/1989 | Yang et al. | 250/339 |
| 5,153,519 | 10/1992 | Wentworth et al. | 324/464 |
| 5,317,271 | 5/1994 | Wentworth et al. | 324/464 |

Primary Examiner—Gerard R. Strecker
Assistant Examiner—Diep Do
Attorney, Agent, or Firm—Gunn & Kuffner

[57] ABSTRACT

A pulsed discharge helium photon ionization detector comprises an elongate cylindrical body having an axial flow path. A helium source is connected to deliver helium flowing along this path. In the helium flow path, transversely positioned, facing electrodes are located to form a spark discharged across the helium flow path wherein the spark interacts with the helium to cause photon ionization. Downstream within view of the spark, a counter flow dopant gas injection tube is positioned to deliver dopant at a reduced flow rate. The dopant is swept back along the helium flow path past a set of electrode rings spaced along the flow path. The interaction of the photon ionization with the dopant creates a base current which can be detected by an electrometer across the terminals. A sample injection tube adds an eluted GC column sample or peak which changes the base current so that eluted sample is measured.

16 Claims, 1 Drawing Sheet

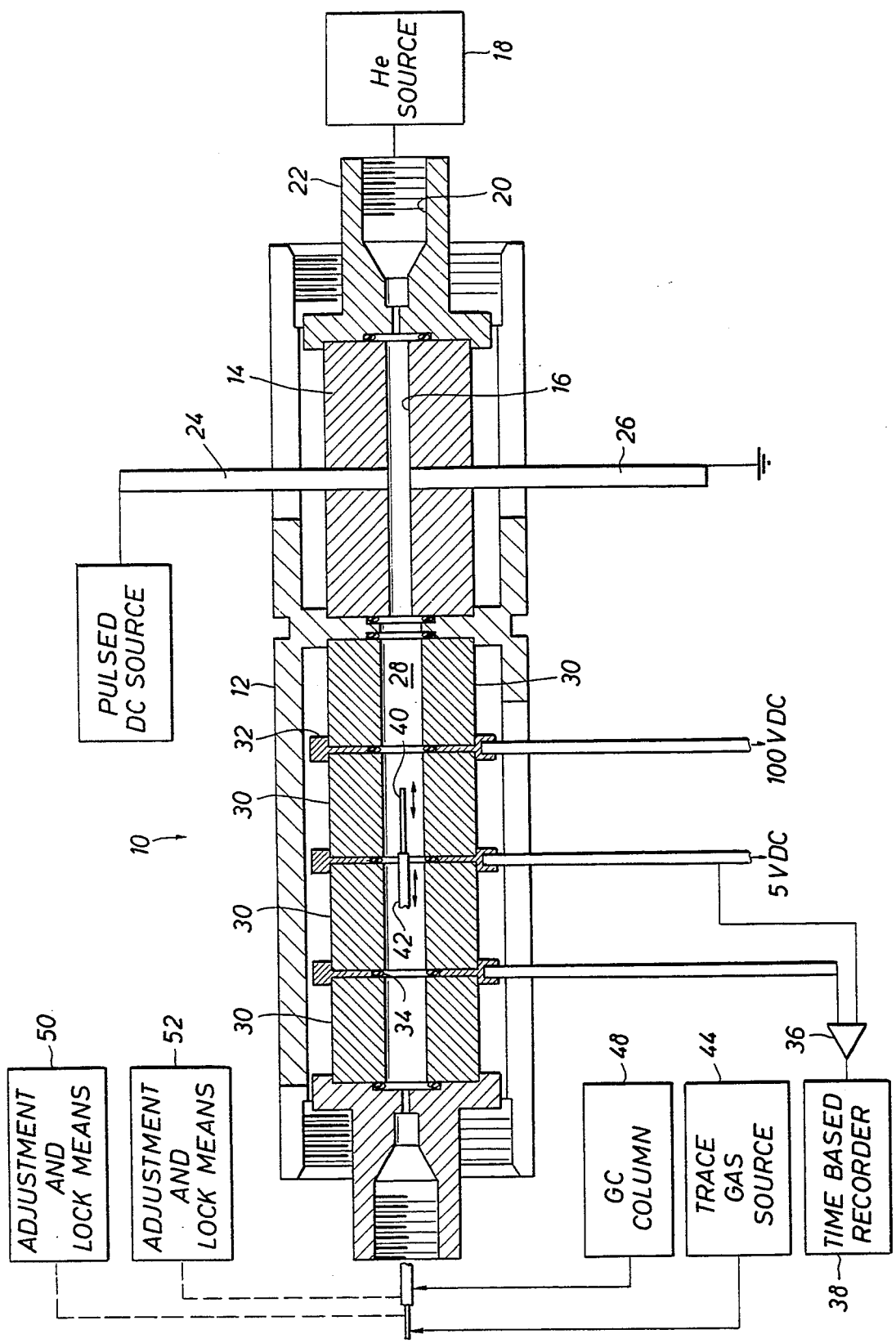

IMPROVED SYSTEM FOR DETECTING COMPOUNDS IN A GASEOUS SAMPLE USING INDUCED PHOTOIONIZATIONS AND ELECTRON CAPTURE DETECTION

The present application is a continuation in part of application Ser. No. 956,632 which was filed on Oct. 5, 1992, now U.S. Pat. No. 5,317,271, which is a continuation in part of application Ser. No. 662,149 which was filed on Feb. 28, 1991, now U.S. Pat. No. 5,153,519.

BACKGROUND OF THE INVENTION

This present disclosure is directed to a spark discharge system which forms photons which are emitted by a pulsed spark discharge across a pair of terminals. The spectra are created by spark interaction with a flow of an inert gas, helium being the preferred gas stream, in the region of the pulsed spark discharge. This creates the photon ionization for use with the sample which will be described.

The improved system of this disclosure utilizes a helium flow through the region of the spark discharge. This helium flow is the only flowing material in the immediate region of the spark. An instrument system is constructed with this so that the helium flow continues through a central axial passage of the equipment to a region having first, second and third ring shaped electrodes surrounding the passage way. The flow is directed to the three ring shaped electrodes so that the flow is able to interact with a sample gas and dopant which is delivered into the flowing helium gas. More specifically, an electron capture detector (ECD hereinafter) is provided by incorporating a trace or dopant gas which is injected into the flow through the three electrodes. The trace gas interacts with the photon ionization emission from the spark to create a charged gas flow. This establishes a current flow between two of the electrodes which current flow can be detected by an electrometer connected across the two electrodes. This current flow defines the base line signal in the equipment. The baseline is adjusted by changing the flow rate of the dopant, by changing the point at which the dopant is introduced, or by also changing or adjusting the position at which the dopant is introduced with respect to the circular electrodes. The baseline condition established is a maximum current flow.

As a test instrument, the ECD utilizes a flow of gas discharged from a gas chromatograph (GC) column or other suitable source. The GC column effluent normally carries with it a carrier gas which is routinely present at a specified flow rate. In addition to that, the GC carrier gas delivers in timed sequence peaks of constituents in a tested sample. For instance, in testing the output of any typical petrochemical product manufactured in large volume, analysis of the purity of the produced product is desirable. One mode of testing is to utilize the GC column which elutes the various constituents in a specific timed sequence dependent on the relative mobility as the sample constituents travel through the GC column. A typical GC column comprises a mobile phase and a stationary phase. The mobile phase comprises a carrier gas such as helium into which sample gas containing one or more compounds are injected. The stationary phase comprises one or more solid constituents within the GC column which exhibit different retention times for the "unknown" sample compounds. The sample gas containing the unknown compounds is injected over a relatively short period of time into the carrier gas flow near the input of the GC column. Sample compounds are retained for different times by the stationary element of the GC, and then subsequently released. Upon release, each type of sample compound is swept by the carrier gas from the GC column and discharged in the form of a "peak" or maxima in concentration in the carrier gas. Retention times, and therefore time separation of the unknown compound peaks, is a function of several factors including the carrier gas flow rate and the type of the stationary phase within the GC column. The result of an injection near the input of a sample gas containing multiple compounds results in the subsequent release, or "eluates", of maxima or peak concentrations of individual compounds at the output of the GC column. Again, time recording of the GC output reflects these elutes as peaks. Stated another way, the GC separates sample compounds by eluting in the form of concentration maxima or peaks in the output carrier gas at varying times, measured from the injection of the composite sample gas. As described, the GC process does not quantify the concentrations of the unknown compounds, but does separate multiple compounds for further analysis using the current ECD invention. By using a series of calibration gases, a fixed flow rate, and a specific fixed phase material, the GC process can be used to identify compound types based upon the time position of the eluted peaks, measured with respect to the injection of the composite gaseous sample. There may be any number of eluted peaks formed by the GC column output which peaks must be detected and quantified. The ECD system is a good technique for peak quantification. Enhanced sensitivity is therefore obtained as the peaks of the sample are passed through the ECD device.

Adjustment of an ECD is somewhat delicate. The present disclosure sets forth an arrangement which can be readily adjusted. In this particular version, the ECD forms a baseline current as a result of photon ionization of helium flowing through the pulsed spark discharge. That creates radiation sufficient to interact with an introduced dopant located strictly in an isolated region downstream from the spark creating electrodes. The electrodes forming the spark are isolated in an atmosphere of helium and therefore have an extended life. Dopant materials introduced elsewhere in the system are introduced at such a low flow rate that they are swept away from the pulsed spark terminals. Moreover, this assures that the pulsed discharge interacts only with the inert helium, not with the dopant or any sample from the GC column. This prevents burning of any compound which might create soot or otherwise form an undesired deposit on the interior of the ECD equipment. Two concentrically positioned tubes are introduced into the ECD equipment. They are inserted into the flowing stream of helium gas which sweeps the area where the spark is formed. In routine operation, the helium flow is typically in the range of about 20–150 milliliters or so. A typical flow is about 100 milliliters. This flow enables the insertion of two concentrically located tubes downstream which introduce additional flow but which gases cannot migrate against the larger helium flow which is significantly larger, perhaps 5 to 50 times larger in volume. One injection tube which is positioned in the ECD chamber delivers a trace or dopant gas. It is a gas which is readily ionized and which interacts with the photon ionization emission from the spark discharge. One example of the trace gas introduced is hydrogen. It interacts readily and is highly mobile, diffusing in the region downstream from the point of introduction. A second tube is utilized to inject an additional flow downstream. The second tube is located so that its discharge is into the hydrogen diffused area so that the GC column effluent is introduced. The GC column effluent is primarily a carrier gas which is neutral electrically. The second tube also discharges the separated peaks from the GC column. Because they are not electrically neutral, they create a current flow variation in comparison with the current flow established in quiescent conditions when only the trace or dopant gas is introduced to the ECD. For that reason, a steady state condition is first established. This occurs when a specified flow rate of the dopant gas is introduced. An example might be an introduction rate of 1 milliliter per minute of hydrogen which is introduced into a flow of 100 milliliters per minute of helium. The discharge from the GC column typically will be something of the same magnitude, perhaps a fraction up to about 2 or 3 milliliters per minute. This is introduced downstream of the dopant introduction point. If the dopant is hydrogen (the most mobile of molecules), then interaction is readily obtained because the hydrogen will diffuse easily through the flowing stream of helium. The hydrogen flow in the quiescent state establishes a current flow which is scaled to a maximum value. Thereafter when a peak is separated by the GC column, the peak constituent delivered into the ECD causes a drop in current. This enables measurement of peak amplitude. As will be understood in the detailed description of current flow in the following paragraph, the peak amplitude creates a current flow drop in the negative direction. Helium ions and free electrons are created when the preferred helium gas flow is exposed to the spark creating electrodes through the reaction $$He = He^+ + e^- \tag{1}$$

where $He^+$ denotes a positively charged He ion and $e^-$ denotes a free electron. After the spark discharge, some of the energy from the free electron flux interacts with neutral helium in the flow gas to form excited helium $He^*$ through the reaction $$e^- + He = He^* + e^- \tag{2}$$

Subsequently, $He^*$ decays by the emission of a photon through the reaction $$He^* = He + photon \tag{3}$$

As dopant gas such as hydrogen is introduced into the chamber, the photons produced by the reaction of Equation (3) interact with the hydrogen to produce H ions and free electrons through the reaction $$photon + H = H^+ + e^- \tag{4}$$

The flow of hydrogen ions and free electrons establish the previously defined base line current of the device. Once an "unknown" compound, denoted generically as "AB", is introduced into the system, the free electrons of Equation (4) can initiate several classes of reactions including $$e^- + AB = (AB)^* + e^- \tag{5}$$

and $$(AB)^* = AB + photon \tag{6}$$

where $(AB)^*$ denotes an excited state of compound AB. Upon introduction of an unknown compound AB, the reaction of Equation (6) competes for some of the electron population under steady state or baseline conditions. As a result, the introduction of a compound AB results in an observed current flow-drop in the ECD system.

Summarizing, the present ECD system utilizes the spark formed across a pair of terminals transverse to the helium flow introduced into the system. Radiation resultant from the photon ionization of the helium creates an interaction downstream with an introduced dopant in small volume. This establishes a first current rate which is the steady state condition for the ECD. Downstream of the dopant introduction point, another introduction point is used to inject the GC column eluted peaks along with the GC column carrier. The first, second and third terminals are utilized having the preferred form of encircling rings about the passage, and an electrometer output provides measurements of the current flow from the ECD. The output signal is typically recorded by a time based recorder.

BRIEF DESCRIPTION OF THE DRAWINGS

So that the manner in which the above cited features, advantages and objects of the present invention are obtained and can be understood in detail, more particular description of the invention, briefly summarized above, may be had by reference to the embodiments thereof which are illustrated in the appended drawings. It is to be noted, however, that the appended drawings illustrate only typical embodiments of the invention and are therefore not to be considered limiting of its scope for the invention may admit to other equally effective embodiments.

This view shows, in section, the internal workings of the ECD of the present disclosure illustrating a helium gas input cooperative with a pair of spaced electrodes and further having a reaction chamber downstream equipped with three circular, ring shaped electrodes and further includes a dopant injection tube and a GC column effluent injection tube located for operation in the ECD.

DETAILED DESCRIPTION OF THE PREFERRED EMBODIMENT

Attention is directed to the only drawing where the numeral 10 identifies the ECD system of this disclosure. It is constructed with an elongate cylindrical housing 12 which contains a cylindrical member 14 which is axially hollow at 16. This forms a passage through which helium is introduced. Helium is the preferred form of gas although other inert gases are known to exist. The helium flows from a regulated helium source 18 which is connected through a regulator (not shown) to deliver helium at a pressure slightly above atmospheric pressure and flowing at a rate of about 20 to about 150 milliliters per minute. This flow is introduced into an industry standard fitting detail 20 formed in a fitting body 22 at one end of the equipment. By means of a suitable externally threaded nut (not shown), the fitting body 22 is held in the illustrated position to assure locking in the ECD apparatus 10. Flow is directed from the fitting 22 into the passage 16. The flow is directed to the axial passage 16 and moves between a pair of spaced electrodes. The electrodes are identified at 24 and 26. They preferably terminate in parallel end faces. More specifically, the parallel end faces are constructed on metal rods having a diameter of about 1/16" and which are spaced with end faces approximately 1/16" across the passage 16. In an optional aspect of this particular embodiment, the electrodes are reduced in diameter to a smaller diameter of about 0.3 mm. This can be obtained by forming the two electrodes 24 and 26 of wire stock of that size. In an alternate aspect, larger electrodes can be used and sharpened points can be formed with that size. As before, it is desirable that the points be located so that the spark is transverse to the gas flow in the passage 16. The two terminals which form the spark define a sharply fixed, narrowly constrained spark on each spark formation so that the spark does not dance around the two electrodes faces, and remains in the form of a straight line. Consequently, it is not necessary to otherwise confine the spark location. It is also not necessary to include any sort of light collimation mechanism. Rather, the light is collimated because the spark definition is relatively narrow and constrained.

The flow passage 16 connects downstream with a larger passage 28. The passage 28 is formed on the interior of a spacer ring 30. Several spacer rings are positioned serially to define the extended passage through which the helium flows. In the preferred embodiment, there are four spacer rings which are separated by three identical electrode rings 32. The electrode rings are provided with an external encircling collar which includes an inwardly directed webbing connecting with an exposed electrode ring 34. The ring 34 is located in the passage 28 and is flush mounted with the passage. It is formed of metal and has an exposed face which is defined by the spacing by adjacent rings 30. Moreover, the several rings 34 serves as first, second and third electrodes for operation of the ECD. The first ring is connected with a negative voltage source and is typically in the range of about 50–250 VDC. As illustrated, approximately −100 VDC will suffice for operation. The next ring is connected with a bias source of about −5 VDC. The third ring is permitted to float. The last two rings provide terminals for an electrometer which measures current flow and which forms an output for a time based recorder. The electrometer 36 is input to a recorder 38. The signal for the recorder 38 will be discussed in some detail.

The system also includes first and second injection tubes. In the preferred embodiment, they are arranged concentric of each other and are positioned axially in the structure. The smaller tube 40 introduces a fixed flow rate of a trace gas or dopant. It is provided by the trace gas source 44. The second of the two concentric tubes 42 is input in the ECD and introduces a flow from the GC column 48. This flow is introduced at a different location. The two injection tubes terminate at different locations. This changes the introduction region, making it adjustable for reasons to be described. The tubes 40 and 42 are moved to and fro with respect to the body of the ECD 10. For this purpose, the tube 40 is moved to a selected or adjustable position and a lock means 50 is then operated to fix the tube at a specified location. In similar fashion, a lock means 52 is used to lock the tube 42 at a specified location. As shown in the drawings, arrows indicate relative movement of the tubes 40 and 42. In the concentric deployment of the two tubes, there is sufficient flow space in the two tubes to introduce the desired flow rate for operation of the equipment. If desired, the tubes can be positioned adjacent to each other and introduce the two gas flows through immediately adjacent small capillary tubes. In another aspect of construction, the tubes can be fixedly located by extending through the spacer rings 30 to position a discharge point approximately at the centerline axis of the equipment. Adjustments however are thought to be advantageous and for that reason, the tubes 40 and 42 are inserted coaxially of the ECD structure which makes it relatively easy to move the tubes left and right as viewed in the drawings.

The gas flow which is introduced into the system moves from right to left. It is substantially greater than the gas flow from the tubes 40 and 42. Therefore the dopant gas and GC column effluent are simply swept along the larger volume of helium in this system. The tube 40 introduced the dopant which is forced to the left by the larger helium flow volume and the dopant gas diffuses in this region. It is available for interaction with the photon ionization from the spark gap. It is one theory of operation of the present system that the photon ionization is created by the transitory existence of spark created diatomic helium molecules which quickly breakdown into single atoms of the inert gas. In this transition a photon of light energy within a relatively broad spectrum is emitted and directed along the passage way 16 and in the chamber 28. By testing with an inserted opaque shutter, the transmission can be stopped which seems to completely stop the photon ionization with the dopant gas. Restated, it appears that light transmission must be obtained so that the photons emitted from the spark region are able to interact with the dopant gas. It is desirable that the dopant gas therefore be within view of the spark. So to speak, the view must be something of a straight line or alternately must include sufficient reflective surfaces to direct the photon ionization emission to the region at which dopant is introduced. In the illustrated construction, no particular reflective materials are required because the use of conventionally available plastic materials is sufficient. To wit, the body 14 and the spacer rings 30 are preferably formed of translucent plastic materials which are readily machined which forms a relatively effective reflective surface. So to speak, a light tunnel is defined, and the light from the spark gap is not able to diffuse through the bodies which form the structure. The light is directed along the passage 16 and into the chamber 28.

The physical spacing from the spark gap at the electrodes to the regions of the first, second and third electrodes is not overly long. Distances are up to about 2 or 3 centimeters have been effectively used. Accordingly, a smaller ECD construction can be used. This is a scale of ECD which is quite effective. If for instance, the chamber 28 is excessively broad, small peaks eluted from the GC column will simply be lost as the peaks diffuse excessively laterally. Therefore the diameter of the chamber 28 is preferably reduced. As the diameter is reduced and the length is reduced, sensitivity to the smaller peaks is enhanced. Sensitivity is also enhanced by proper positioning of the tip of the two injection tubes 40 and 42. The tube 40 is moved to introduce the dopant gas approximately even with the first electrode. The second tube 42 terminates approximately even with the second electrode. This enables the electric field established by the first and second electrodes to interact with the dopant gas and also the eluted peak gases from the GC column to have spaced to interact with the drifting electrons as the gases are swept to the left of the single drawing. A steady state current is established with a particular flow rate of dopant gas from the injection tube 40. That is adjusted so that a maximum value is established. This adjustment can be changed by changing the flow rate of the dopant gas, by moving the location of the injection tube 40 with respect to the first and second electrodes, and by changing the velocity of the helium gas through the system. Spacing of the electrodes can also make a difference in this aspect. Since however the electrodes are structurally fixed in location, for a given construction of ECD, adjustments are more readily made by moving the tube 40 or by changing the flow rate of the helium through the system. In any case, a specified base level of current is established, recalling that this is a maximum current flow.

For calibration, a controlled quantity of eluted sample gas is introduced through the tube 42. This mimics a peak which is separated by the conventional operation of the GC column. This separated peak is permitted to pass through the system. When it does, it interacts with electrons in the flowing helium carrier gas associated from the ionized dopant gas to change the current. Restated, the baseline current is reduced in proportion to the size of the sample which is introduced for calibration purposes. That enables one to calibrate the equipment recalling that a negative going signal is formed. In other words, the baseline value is relatively high but that current is decreased when a GC eluted peak passes through the system.

In regular operation of this equipment the two tubes may be moved to a particular location and locked in location. Alternately, the two tubes can be adjusted from time to time depending on the system requirements. As a generalization, system operations remains substantially unaltered even though there may be variations in the pulse rate for the pulsed DC source which is connected to the terminal 24. Moreover, it is operated to form serial isolated, individual DC pulses. The various pulses are delivered at a control rate typically in the range of 10–10,000 individual pulses per second. The duty cycle is preferably one in which very narrow pulses are formed without ringing. Narrow pulses typically are preferred having a pulse width of perhaps 10 microseconds or less. The voltage is sufficient to cause breakdown and therefore the formation of the visible spark. While the foregoing is directed to the preferred embodiment, the scope is determined by the claims which follow.

What is claimed is:

1. An electron capture detector comprising:
   (a) a closed chamber having a helium flow inlet and spaced helium flow outlet to enable helium flow therethrough;
   (b) spaced electrodes cooperating with a DC current source thereby permitting an electrical arc to be formed between said spaced electrodes defining a spark thereacross, said spaced electrodes being positioned in said chamber to form a spark gap across said helium flow through said chamber;
   (c) a dopant gas source connected to said chamber to provide a controlled dopant flow at continuously adjustable locations within said chamber thereby forming a base current within said chamber where said base current is initiated by said spark across said spark gap;
   (d) a sample gas source connected to said chamber to provide sample gas containing eluted compounds of unknown concentration;
   (e) current detector electrode means spaced along the axis of said chamber for collection of current formed as a result of said spark across said spark gap wherein said helium flow moves toward said current detector electrodes to enable currents to be formed and measured indicative of one or more said eluted sample compound concentrations in said chamber and dependent on the dopant gas in said helium; and
   (f) wherein said current detector electrode means measures the eluted sample concentrations in said chamber by changes in said current flow.

2. The apparatus of claim 1 wherein the dopant gas is hydrogen.

3. The apparatus of claim 1 wherein said current detector electrode means are axially spaced downstream from said spark gap formed by said spaced electrodes.

4. The apparatus of claim 1 wherein said dopant gas is introduced into said chamber by a dopant gas tube with one end of said dopant gas tube connected to a source of dopant gas external to said chamber and the second open end of said dopant gas tube terminating within said chamber downstream of said spaced electrodes which form said spark gap.

5. The apparatus of claim 4 wherein said chamber encloses an open end of said dopant gas tube at a location therein so that said helium flow mixes with the dopant gas and said dopant gas forms an electrical current resultant from the spark at said spaced electrodes.

6. The apparatus of claim 5 wherein said chamber is constructed with an elongate helium gas flow passage and said passage directs helium flow to said current electrode detector means and also directs photon emissions from said spark to interact with dopant gas to form an electrical current.

7. The apparatus of claim 6 including a sample source external to said chamber and a sample carrier gas tube positioned in said chamber and a concentric with said dopant gas tube, and wherein helium gas flow is from said inlet to said outlet; and
   wherein the opening of said dopant gas tube is positioned to introduce dopant gas downstream of said spaced electrodes which form said spark gap and wherein the opening of said sample carrier gas tube is downstream of the opening of said dopant gas tube so that said dopant gas flows downstream to mix with said eluted sample and sample gas carrier.

8. The apparatus of claim 7 wherein said chamber is an elongate, open, hollow passage in a surrounding housing, and said dopant gas tube is located in said chamber.

9. The apparatus of claim 6 wherein the axes of said source carrier gas tubes and said dopant gas tubes are parallel within said chamber and said axes are essentially parallel to the axis of said chamber.

10. A method of measuring an eluted sample from a GC column sample source comprising the steps of:
   (a) flowing an inert gas from an inlet to an outlet in a chamber through a spark gap positioned near said inlet;
   (b) forming a spark to excite the inert gas, said spark being formed by an electrical discharge across two electrodes which cooperate with a pulsed DC source and are spaced to form a spark gap;

(c) at continuously adjustable locations downstream in said chamber, introducing a dopant gas into said inert gas flow to enable said dopant gas to respond to the excited inert gas and thereby form an electric current flow in said chamber;

(d) further downstream from the point of introduction of said dopant gas in said chamber introducing an eluted sample from a sample source which is mixed with said inert gas and said dopant gas to cause a variation in said electric current flow in said flowing gases related to eluted sample quantity; and (e) determining the concentration of said eluted samples from a measure of said electric current flow.

11. The method of claim 10 further including the step of measuring current flow solely from dopant gas flow to obtain a base current measurement, and then measuring current reduction resultant from eluted sample.

12. The method of claim 11 further including the step of measuring current associated with an eluted sample in said chamber, and then measuring associated current flow with a subsequent eluted sample in said chamber.

13. The method of claim 12 wherein the step of measuring current includes the initial step of positioning current responsive electrodes in said chamber at a selected downstream location so that current is measured.

14. The method of claim 13 including the step of measuring current between two measuring electrodes in said chamber.

15. The method of claim 14 wherein the dopant gas is hydrogen, and the dopant gas reacts with photons emitted resulting from the spark to create a current flow in the dopant gas in said chamber.

16. The method of claim 15 wherein spark emitted photons are directed by said chamber into the dopant gas to disassociate electrons to create the current flow.

* * * * *

UNITED STATES PATENT AND TRADEMARK OFFICE
CERTIFICATE OF CORRECTION

PATENT NO. : 5,394,090

DATED : February 28, 1995

INVENTOR(S) : Wayne E. Wentworth and Stanley D. Stearns

It is certified that error appears in the above-indentified patent and that said Letters Patent is hereby corrected as shown below:

On the title page item [76], change "Stanley D. Sterns" to --Stanley D. Stearns--.

Signed and Sealed this

Sixth Day of June, 1995

*Attest:*

BRUCE LEHMAN

*Attesting Officer*       *Commissioner of Patents and Trademarks*